United States Patent
Wu et al.

(10) Patent No.: US 12,415,037 B2
(45) Date of Patent: Sep. 16, 2025

(54) NEEDLELESS INJECTION DEVICE AND METHOD USING THE SAME

(71) Applicants: Rongrong Wu, El Sobrante, CA (US); Suheng Liu, Wuhan (CN)

(72) Inventors: Rongrong Wu, El Sobrante, CA (US); Suheng Liu, Wuhan (CN)

( * ) Notice: Subject to any disclaimer, the term of this patent is extended or adjusted under 35 U.S.C. 154(b) by 1280 days.

(21) Appl. No.: 17/151,200

(22) Filed: Jan. 17, 2021

(65) Prior Publication Data
US 2022/0226578 A1  Jul. 21, 2022

(51) Int. Cl.
*A61M 5/30* (2006.01)
*A61M 5/24* (2006.01)
*A61M 5/31* (2006.01)

(52) U.S. Cl.
CPC ............... *A61M 5/30* (2013.01); *A61M 5/24* (2013.01); *A61M 2005/2444* (2013.01); *A61M 2005/2477* (2013.01); *A61M 2005/3128* (2013.01)

(58) Field of Classification Search
CPC .......... A61M 5/31565; A61M 5/31578; A61M 5/31585; A61M 2005/14506; A61M 5/145; A61M 60/462; A61M 60/459; A61M 60/486; A61M 60/489; A61M 60/492; A61M 5/30
See application file for complete search history.

(56) References Cited

U.S. PATENT DOCUMENTS

| | | | |
|---|---|---|---|
| 2003/0083611 A1* | 5/2003 | Angel | F03G 7/065 604/68 |
| 2024/0181162 A1* | 6/2024 | Lee | A61M 5/30 |

FOREIGN PATENT DOCUMENTS

| | | |
|---|---|---|
| CN | 203291417 U | 11/2013 |
| CN | 205145307 U | 4/2016 |

* cited by examiner

*Primary Examiner* — Lauren P Farrar

(57) ABSTRACT

The present disclosure provides a needleless injection device and methods to use the same. The needleless injection device comprises a first slider, a second slider, a driving unit to move the first and second sliders, and an ampoule injection tube. The driving unit controls the movement of the first and second sliders such that the value of the combined momentum of the first and second sliders is substantially zero, and the movement of the first and second slider injects the liquid from the ampoule injection tube into a subject.

5 Claims, 11 Drawing Sheets

NEEDLELESS INJECTION DEVICE AND METHOD USING THE SAME

FIELD OF INVENTION

The present invention generally relates to medical device, and, more particularly, relates to a needleless injection device.

BACKGROUND OF THE INVENTION

The needleless injection technology relates to directly injecting a liquid or fluid, such as a medicine, into body of the subject through his skin. This injection can be done by using a needleless injection device and forming a thin liquid flow under high pressure so that the thin liquid flow can penetrate the skin instantly to reach the subcutaneous part. Needleless injection devices need very high pressure placed on the liquid to be injected. High kinetic energy can be obtained by driving a slider mounted on a needleless injection device at high speed to hit the syringe part of the device. The slider with high kinetic energy can strike the piston of the needleless injection device to transfer the momentum of the slider to the liquid or fluid in the syringe part of the device. Subsequently the liquid is ejected out of the device with high speed to complete the injection process.

The kinetic energy used in the injection process in the needleless injection device can be partially used for generating high pressure to the liquid, and the residual kinetic energy can generate recoil motions to the needleless injection device. Recoil may cause severe, momentary vibration of the needleless injection device, which is in turn transmitted to the subject and/or the technician using the device. Such recoil motion may be transmitted to the people nearby, particularly to the subject to be treated. The may cause discomfort to the subject.

SUMMARY OF THE INVENTION

One aspect of the present disclosure provides a needleless injection device, comprising: a housing; a first slider disposed in the housing and movable along an axis; a second slider disposed in the housing and movable along the axis; an ampoule injection tube; and a driving unit configured to move the first slider and the second slider in opposite directions along the axis, characterized in that the value of the combined momentum of the first slider and the second slider is substantially zero under the control of the driving unit.

In some embodiments of aspects provided herein, the device further comprises: a piston configured to slide inside the ampoule injection tube and interact with the first slider, the second slider, or both the first and second slider.

In some embodiments of aspects provided herein, the device further comprises: a center injection shaft attached to the second slider and configured to interact with the piston, wherein the center injection shaft is configured to contact the piston when the second slider moves away from the first slider; or an overhead injection shaft attached to the first slider and configured to interact with the piston, wherein the other injection shaft is configured to contact the piston when the first slider moves toward the second slider.

In some embodiments of aspects provided herein, the driving unit further comprises a momentum spring between the first slider and the second slider, the housing comprises: a first opening on one end of the housing along the axis; a second opening on the other end of the housing along the axis; an attached first steel marble; and an attached second steel marble; wherein the first slider is a first disk comprising a first curved surface, and there is a first groove on the first curved surface; wherein the first groove is configured to mate with the attached first steel marble when the momentum spring is compressed; wherein the second slider is a second disk comprising a second curved surface, and there is a second groove on the second curved surface; and wherein the second groove is configured to mate with the attached second steel marble when the momentum spring is compressed.

In some embodiments of aspects provided herein, the driving unit further comprises a momentum spring between the first slider and the second slider; the first slider comprises a first rod pointing outward and perpendicular to the axis, the first rod is configured to move the first slider along the axis; the second slider comprises a second rod pointing outward and perpendicular to the axis, the second rod is configured to move the second slider along the axis; the first rod and the second rods are on the same side relative to the first slider and the second slider, and aligned substantially within in a plane comprising the axis; the needleless injection device further comprises: a rotatable shaft comprising a curved surface comprising a symmetric groove, wherein the symmetric groove is configured to engage with the first and second rod, thereby moving the first and second rod along the axis when the rotatable shaft is rotated, wherein the symmetric groove comprises: a first nadir, a first apex, a second apex, and a second nadir sequentially along a second axis in that order; wherein the second axis parallels the first axis; wherein the first nadir and the first apex are connected with a first plane comprising the second axis and a first spiral plane revolving a rotational axis for the shaft; and wherein the second nadir and the second apex are connected with a second plane comprising the second axis and a second spiral plane revolving the rotational axis for the shaft; and a gear motor configured to rotate the rotatable shaft. In some embodiments of aspects provided therein, the rotatable shaft further comprises sound-absorbing materials near the first nadir and the second nadir.

In some embodiments of aspects provided herein, the driving unit further comprises: a first positioning spring between the first slider and the second slider; a second positioning spring between the first slider and one end of the housing; a third positioning spring between the second slider and the other end of the housing; an inlet in fluid communication with a first space surrounding the first positioning spring; a first outlet in fluid communication with a second space surrounding the second positioning spring; and a second outlet in fluid communication with a third space surrounding the third positioning spring.

In some embodiments of aspects provided herein, the driving unit further comprises: a first electromagnet affixed inside the housing and disposed between the first slider and one end of the housing; and a second electromagnet affixed inside the housing and disposed between the second slider and the other end of the housing, thereby the first slider and the second slider are disposed between the first electromagnet and the second electromagnet; wherein the first slider comprises a first permanent magnetic core with a first connection rod configured to slide through the hollow center of the first electromagnet; wherein a first buffer spring is disposed between the first permanent magnetic core and the first electromagnet; wherein the second slider is a second permanent magnetic core connected to the center injection shaft through the hollow center of the second electromagnet;

and wherein a second buffer spring is disposed between the second permanent magnetic core and the second electromagnet.

In some embodiments of aspects provided herein, the driving unit further comprises: a connection disk disposed inside the housing and connected with a center injection shaft pointing toward the piston; an upper connection arm connecting the connection disk with the first slider; a lower connection arm connecting the connection disk with the first slider; a first voice coil configured to become a first electromagnet, the first voice coil disposed between the first slider and the second slider; a second voice coil configured to become a second electromagnet, the second voice coil disposed between the first voice coil and the second slider; the first slider comprises a first permanent magnet; and the second slider comprises a second permanent magnet.

In some embodiments of aspects provided herein, the driving unit further comprises: a pouch disposed between the first slider and the second slider, the pouch comprising an outlet and a fluid, wherein the pouch is configured to engage with the center injection shaft via the fluid.

In some embodiments of aspects provided herein, the device further comprises: a medicine storage container; a pouch disposed between the first slider and the second slider, the pouch comprising: an inlet; and an outlet; a first conduit connecting the medicine storage container with the inlet of the pouch via a first check valve; and a second conduit connecting the outlet of the pouch with the ampoule injection tube via a second check valve.

In some embodiments of aspects provided herein, the ampoule injection tube is along the axis, and wherein the second slider is positioned between the first slider and the piston.

In some embodiments of aspects provided herein, the ampoule injection tube is not along the axis.

Another aspect of the present disclosure provides a needleless injection device, comprising: a housing; a first slider disposed in the housing and movable along an axis; a second slider disposed in the housing and movable along the axis; and an ampoule injection tube substantially perpendicular to the axis, the ampoule injection tube comprising: a chamber disposed between the first and second sliders; a lower check valve in fluid communication with the chamber; and an ampoule injection port in fluid communication with the lower check valve; a first striking core movable along the axis and configured to engage with the chamber of the ampoule injection tube, wherein the first striking core is between the first slider and the chamber; a second striking core movable along the axis and configured to engage with the chamber of the ampoule injection tube, and wherein the second striking cores is between the chamber and the second slider; and a driving unit configured to move the first slider and the second slider in opposite directions along the axis; wherein the first slider is configured to engage with the first striking core, wherein the second slider is configured to engage with the second striking core.

In some embodiments of aspects provided herein, the device further comprises: a medicine storage container in fluid communication with the ampoule injection tube via an upper check valve.

Still another aspect of the present disclosure provides a needleless injection device, comprising: a housing; a first slider disposed in the housing and movable along an axis; a second slider disposed in the housing and movable along the axis; and an ampoule injection tube substantially perpendicular to the axis, the ampoule injection tube comprising: a chamber disposed between the first and second sliders; an expandable pouch disposed in the chamber; a pressure-limit valve in fluid communication with the pouch; and an ampoule injection port in fluid communication with the pressure-limit valve; a first striking core movable along the axis and configured to engage with the expandable pouch, wherein the first striking core is between the first slider and the expandable pouch; a second striking core movable along the axis and configured to engage with the expandable pouch, and wherein the second striking cores is between the expandable pouch and the second slider; and a driving unit configured to move the first slider and the second slider in opposite directions along the axis; wherein the first slider is configured to engage with the first striking core, wherein the second slider is configured to engage with the second striking core.

In some embodiments of aspects provided herein, the device further comprises: a medicine storage container; and a needle in fluid communication with the medicine storage container; wherein the needle is in fluid communication with the expandable pouch via an upper check valve.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

Figure 1:
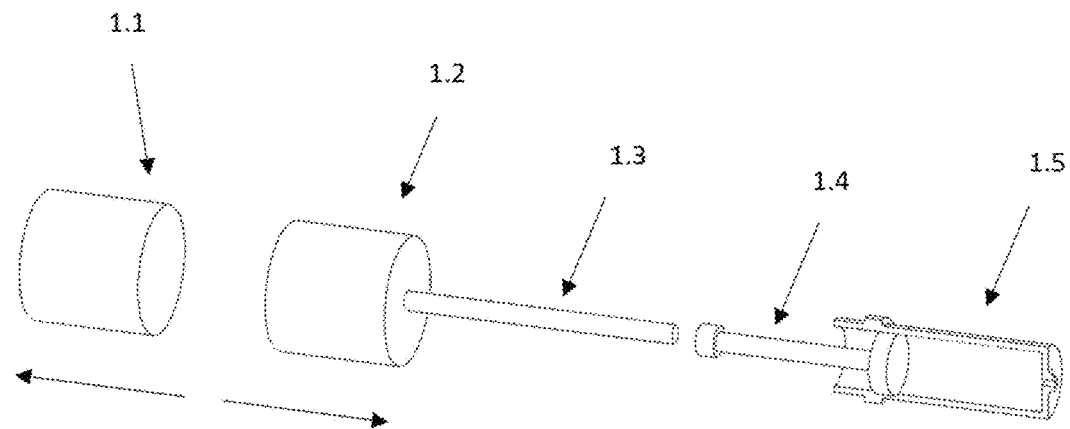
FIG. 1 depicts a schematic structural diagram of a needleless injection device according to an embodiment of the present invention.

Before proceeding with the detailed description, it is to be appreciated that the following detailed description is merely exemplary in nature and is not intended to limit the invention or the application and uses thereof. Hence, although the present disclosure is, for convenience of explanation, depicted and described as shown in certain illustrative embodiments, it will be appreciated that it can be implemented in various other types of embodiments and equivalents, and in various other systems and environments. Furthermore, there is no intention to be bound by any theory presented in the preceding background or the following detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the "present disclosure" or "present application" refers to any one of the embodiments of the disclosure described herein, and any equivalents thereof. Furthermore, reference to various feature(s) of the "present disclosure" or "present application" throughout this document does not mean that all claimed embodiments or methods must include the referenced feature(s).

NUMERALS 1.1 First slider
1.2 Second slider
1.3 Center injection shaft
1.4 Piston
1.5 Ampoule injection tube
1.6 Upper connection arm
1.7 Lower connection arm
1.8 Connection disk
1.9 Pouch
1.10 Conduit
1.11 Reset spring
1.12 Third check valve (pouch)
1.13 Left striking core
1.14 Right striking core
1.15 Expandable pouch
1.51 Ampoule injection port
1.52 Upper check valve
1.53 Lower check valve
1.54 Pressure-limit valve
2.1 Overhead injection shaft
3.1 First opening
3.2 First steel marble
3.3 Second steel marble
3.4 Second opening
3.5 Piston
3.6 First groove
3.7 Momentum spring
3.8 Second groove
3.9 Injection body
5.1 Gear motor
5.2 First rod
5.3 Second rod
5.4 First nadir
5.5 First apex
5.6 Shaft (with a symmetric groove)
5.7 Second apex
5.8 Second nadir
7.1 First positioning spring
7.2 Second positioning spring
7.3 Third positioning spring
7.4 Inlet
7.5 First outlet
7.6 Second outlet
9.1 First electromagnet
9.2 First buffer spring
9.3 First permanent magnetic core
9.4 Distance of separation
9.5 Second permanent magnetic core
9.6 Second buffer spring
9.7 Second electromagnet
10 First voice coil
11 Second voice coil
11.1 Medicine storage container
11.2 First Check valve (for medicine storage container)

11.3 Shaft (for resettable measurement container)
11.4 Resetting spring (for the shaft for measurement container)
11.5 Resettable measurement container
11.6 Second check valve (for resettable measurement container)
12 Conduit
13 Liquid storage container
14 Needle
1400 Needleless injection device
1500 Continuous Needleless injection device
1600 Continuous Needleless injection device
1700 Continuous Needleless injection device
1800 Continuous Needleless injection device

DEFINITIONS

As used herein, the singular forms "a," "an" and "the" include plural referents unless the context clearly dictates otherwise. Thus, for example, reference to "a molecule" includes a plurality of such molecules, and the like.

The term "about" or "nearly" as used herein generally refers to within +/−15%, 10%, 9%, 8%, 7%, 6%, 5%, 4%, 3%, 2%, or 1% of the designated amount.

As used herein, the term "substantially" generally refers to the qualitative condition of exhibiting total or near-total extent or degree of a characteristic or property of interest. One of ordinary skill in the mechanical arts will understand that mechanical phenomena rarely, if ever, go to completion and/or proceed to completeness or achieve or avoid an absolute result. The term "substantially" is therefore used herein to capture the potential lack of completeness inherent in many mechanical phenomena.

To appreciate the features and advantages of preferred apparatuses and methods in accordance with the present disclosure, the reader is referred to the appended FIGS. 1-18 in conjunction with the following discussion. It is to be understood that the drawings are diagrammatic and schematic representations only and are neither limiting of the scope of the present disclosure nor necessarily drawn to scale. Unless stated otherwise, the same numeral refers to the same element in the specification and drawings of the present disclosure.

Figure 2:
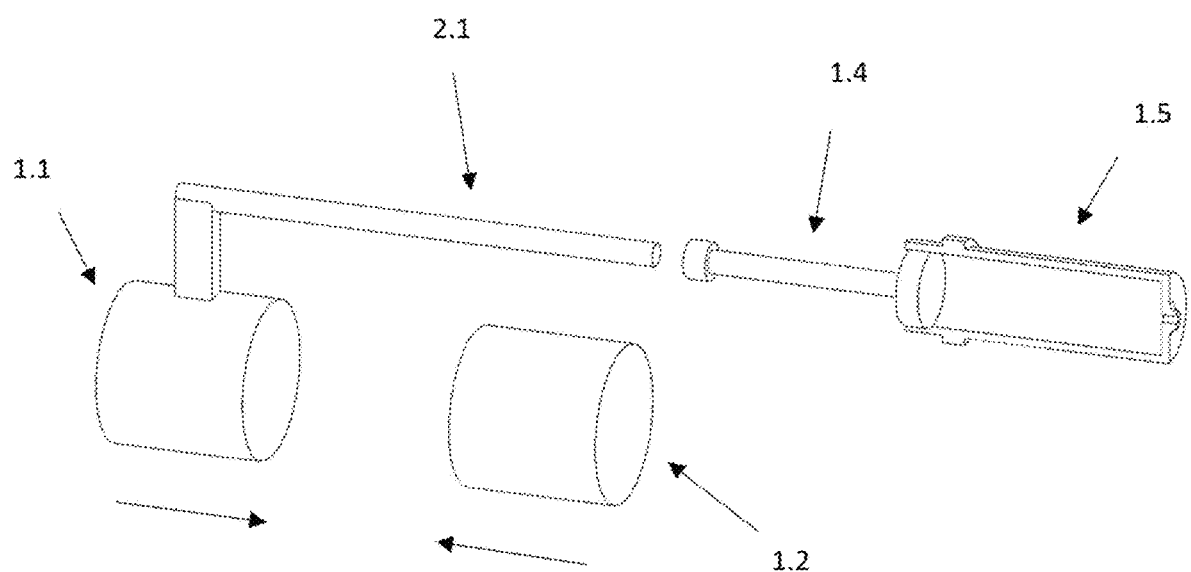
FIG. 2 depicts a schematic structural diagram of a needleless injection device according to another embodiment of the present invention.

The invention provides a needleless injection device configured to reduce or eliminate recoil momentum. As shown in FIG. 1 and FIG. 2, an embodiment of the present invention provides a needleless injection device, which includes a housing, first and second sliders (1.1, 1.2) disposed in the housing, an ampoule injection tube 1.5, a piston 1.4 slidably disposed in the ampoule injection tube 1.5, and a driving unit. The first and second sliders (1.1, 1.2) can push the piston 1.4 in the ampoule injection tube 1.5 under the control of the driving unit, and the piston 1.4 further presses the liquid in the ampoule injection tube 1.5 to complete the injection. The driving unit can control the movement of the first and second sliders such that the value of the combined momentum of them can be substantially zero, i.e., there can be little or no recoil after the rejection.

As shown in FIG. 1, the first and second sliders (1.1, 1.2) can be moving away from each other. The second slider 1.2 can comprise a center injection shaft 1.3 configured to interact with the piston 1.4. When the first and second sliders (1.1, 1.2) are moving away from each other, the second slider 1.2 can drive the center injection shaft 1.3 to push the piston 1.4 within the ampoule injection tube 1.5. The piston 1.4 can further push the liquid in the ampoule injection tube 1.5 to complete the injection function. As shown in FIG. 2, the first and second sliders (1.1, 1.2) can move towards each other. The overhead injection shaft 2.1 on the first slider 1.1 is configured to interact with the piston 1.4. When the first and second sliders (1.1, 1.2) move towards each other, the first slider 1.1 moves towards the second slider 1.2 so as to drive the overhead injection shaft 2.1 to push the piston 1.4 within the ampoule injection tube 1.5. The piston 1.4 can further push the liquid in the ampoule injection tube 1.5 to complete the injection function.

The mass of the first and second sliders (1.1, 1.2) can be adjusted as desired to produce the desirable effect of substantially zero combined momentum. Further, other factors, such as, for example, motion initiation time, motion driving force, motion resistance, motion distance, termination time and the like of the first and second sliders (1.1, 1.2) can be adjusted by the technician and/or controlled by the driving unit, so that the value of the combined momentum of the first and second sliders can be substantially zero when the first and second sliders move substantially simultaneously.

EXAMPLE 1

Figure 3:
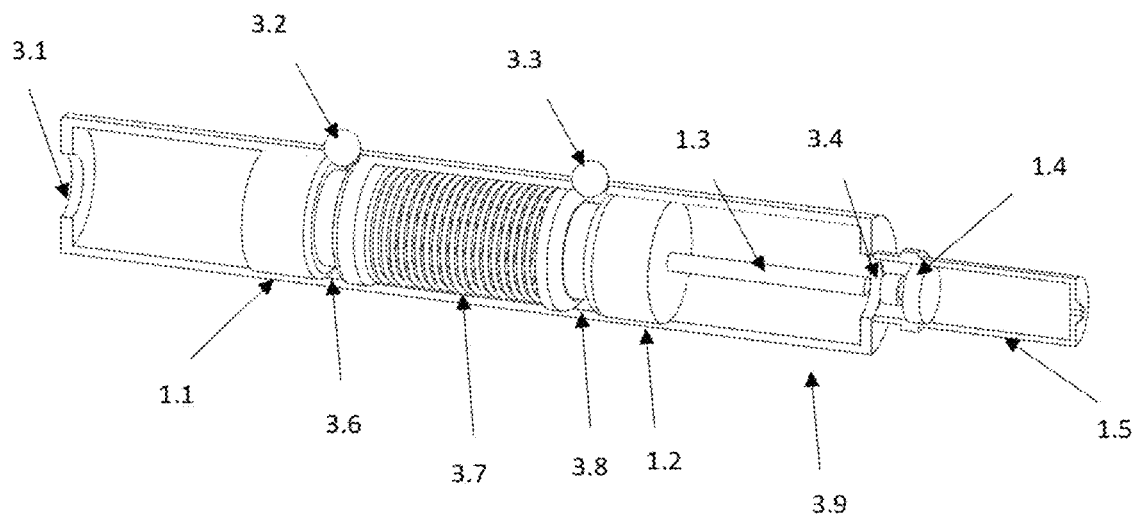
FIG. 3 depicts a schematic structural diagram of a needleless injection device according to an embodiment of the present invention when the momentum spring is compressed.
Figure 4:
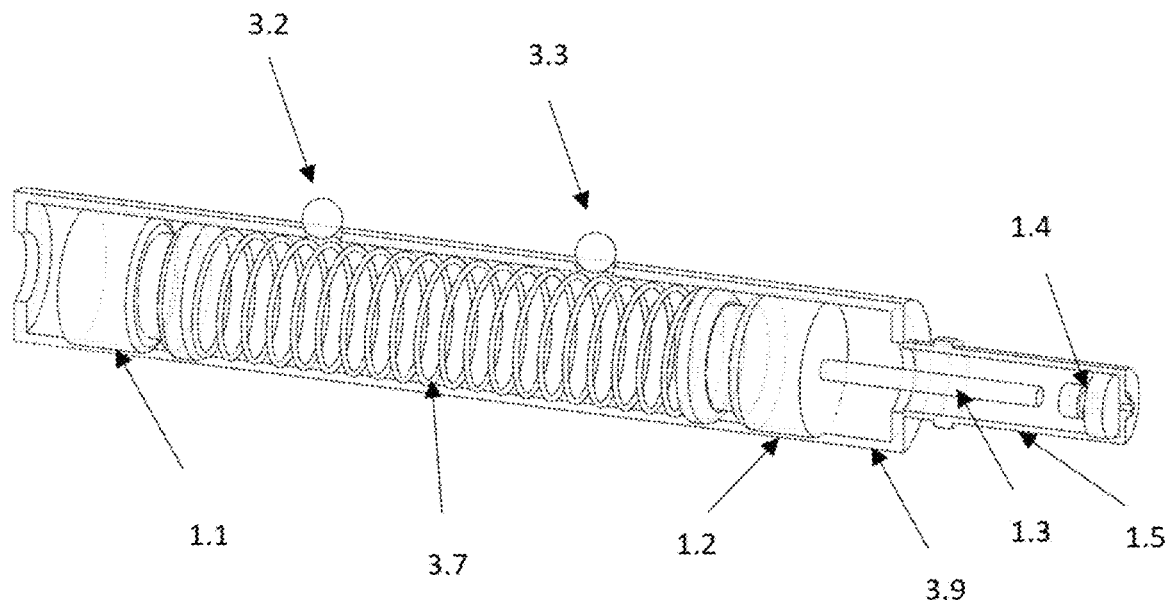
FIG. 4 depicts a schematic structural diagram of a needleless injection device according to an embodiment of the present invention when the momentum spring is relaxed.

FIGS. 3 and 4 show an embodiment of a driving unit which is a manual system using a compression spring. In this embodiment, the driving unit comprises a momentum spring 3.7 installed between the first slider 1.1 and the second slider 1.2, and a controller for confining and releasing the momentum spring 3.7. The momentum spring 3.7 can be compressed after the first slider 1.1 and the second slider 1.2 are both compressed. Then the momentum spring 3.7 is confined and restricted by the controller to maintain an energy storage state. When an injection is needed, the momentum spring 3.7 can be released by controller. The elastic energy stored in the momentum spring 3.7 can be released so as to drive the first slider 1.1 and the second slider 1.2 to move away from each other, as shown in FIG. 1. The center injection shaft 1.3 on the second slider 1.2 can push the piston 1.4 within the injection tube 1.5, thereby pushing the liquid in the ampoule injection tube 1.5 to complete the injection.

In one embodiment, the controller comprises a first groove 3.6 on the first slider 1.1 and a second groove 3.8 on the second slider 1.2; a first steel marble 3.2 configured to mate with the first groove 3.6, a second steel marble 3.3 configured to mate with the second groove 3.8. The steel marbles (3.2, 3.3) are attached to the inside of the housing. The first and second sliders (1.1, 1.2) are disposed in the housing. The first opening 3.1 is at one end of the housing while the second opening 3.4 is at the other end of the housing. An technician can insert auxiliary devices, such as, for example, sticks or a rods, with the appropriate dimension to be inserted through the first opening 3.1 and the second opening 3.4, and compress the momentum spring 3.7 using the sticks or rods. When the momentum spring is compressed, the first and second sliders (1.1, 1.2) can move towards each other. Then the first and second steel marbles (3.2, 3.3) can mate with first and second grooves (3.6, 3.8), respectively, thereby restricting the movement of the momentum spring 3.7 inside the housing.

As shown in FIG. 4, After the operator releases the steel marbles (3.2, 3.3) at the same time, the momentum spring 3.7 can expand and the stored energy can be released. The first and second sliders (1.1, 1.2) can move away from each other, so as to drive the center injection shaft 1.3 to push the piston 1.4 within the ampoule syringe 1.5. The piston 1.4 can push the liquid in the ampoule syringe 1.5 to complete the injection function. The first and second sliders (1.1, 1.2) may not contact with the two ends of the injection body 3.9 during the movement. The kinetic energy of the sliders moving away from each other can be counteracted by the damping action of the momentum spring 3.7, thereby the first and second sliders (1.1 and 1.2) can stop moving before reaching the ends of the injection body 3.9. Consequently, the momentum of the sliders is not transmitted to the needleless injection device. The discomfort to a user can be avoided.

EXAMPLE 2

Figure 5:
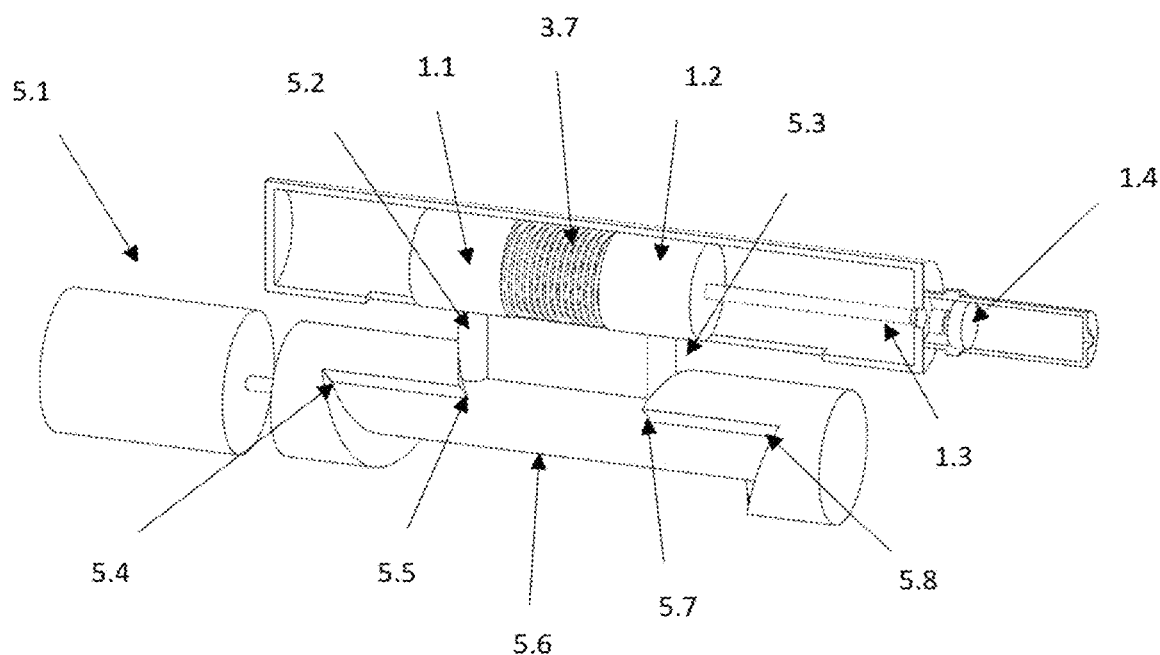
FIG. 5 depicts a schematic structural diagram of a needleless injection device according to an embodiment of the present invention when the momentum spring is compressed in the presence of a rotatable shaft.
Figure 6:
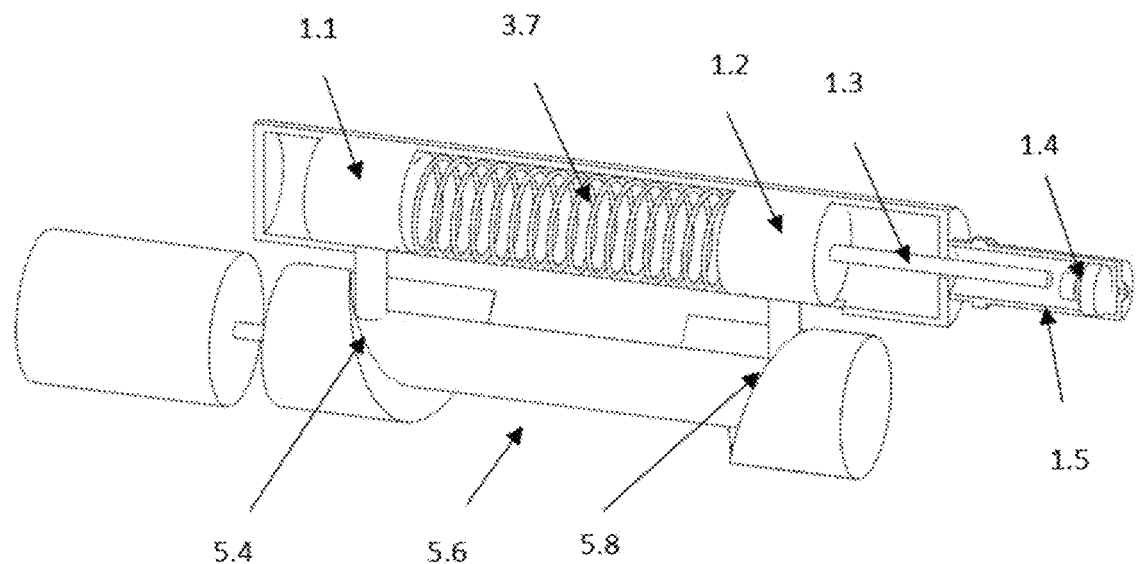
FIG. 6 depicts 5 depicts a schematic structural diagram of a needleless injection device according to another embodiment of the present invention when the momentum spring is relaxed in the presence of a rotatable shaft.

FIGS. 5 and 6 show an embodiment of an electrical system using a compression spring. The driving unit comprises a momentum spring 3.7 disposed between a first slider 1.1 and a second slider 1.2, a first rod 5.2 attached to the first slider 1.1 and a second rod 5.3 attached to the second slider 1.2, a shaft 5.6 and a gear motor 5.1 configured to rotate the shaft 5.6.

The shaft 5.6 comprises a symmetric groove comprising: a first nadir 5.4, a first apex 5.5, a second apex 5.7, and a second nadir 5.8 sequentially along a second axis in that order; the second axis parallels the first axis; the first nadir 5.4 and the first apex 5.5 are connected with (i) a first plane comprising the second axis, and (ii) a first spiral plane revolving a rotational axis for the shaft 5.6; and the second nadir 5.7 and the second apex 5.8 are connected with (i) a second plane comprising the second axis, and (ii) a second spiral plane revolving the rotational axis for the shaft.

As shown in FIG. 5, when the first rod 5.2 is at or near the first apex 5.5 and the second rod 5.3 is at or near the second apex 5.7, the momentum spring 3.7 is compressed. When the gear motor rotates the shaft 5.6 clockwise when viewed from the second slider 1.2 toward the first slider 1.1, the first rod 5.2 can suddenly drop to the first nadir 5.4 while the second rod 5.3 can drop to the second nadir 5.8, thereby causing the first and second sliders moving away from each other and releasing the momentum spring 3.7. The piston 1.4 can push the liquid in the ampoule injection tube 1.5 to complete the injection. Thereafter, the gear motor can keep rotating the shaft clockwise, thereby pushing the first rod 5.2 back to the first apex 5.5 and the second rod 5.3 back to the second apex 5.7, moving the first and second sliders towards each other, and completing a cycle.

After the first and second sliders (1.1, 1.2) push the center injection shaft 1.3, the first and second rods (5.2, 5.3) slide to the first and second nadirs (5.4, 5.8) at two ends of the shaft 5.6, so that the first and second sliders (1.1, 1.2) are limited to move towards two ends of the injector device, and do not contact the two ends of the injection device with momentum. The kinetic energy of the separated sliders is counteracted by the damping action of the momentum spring 3.7, so that the sliders stops moving before reaching the ends of the injection body 3.9. Hence, the kinetic energy of the sliders is not transmitted to the needleless injection device. No discomfort to the subject.

Preferably, the first and second nadirs (5.4, 5.8) of the shaft 5.6 can be provided with sound-absorbing and energy-absorbing materials such that the impact sounds when the first and second rods (5.2, 5.3) contact the first and second nadirs (5.4, 5.8) can be reduced. In addition, by controlling the thickness of the sound-absorbing materials, the time when the first and second sliders (1.1, 1.2) stop can be synchronized such that their combined momentum is minimal or close to zero. The gear motor can provide continuous rotation, so that multiple successive injections by the needleless injection devices are possible.

EXAMPLE 3

Figure 7:
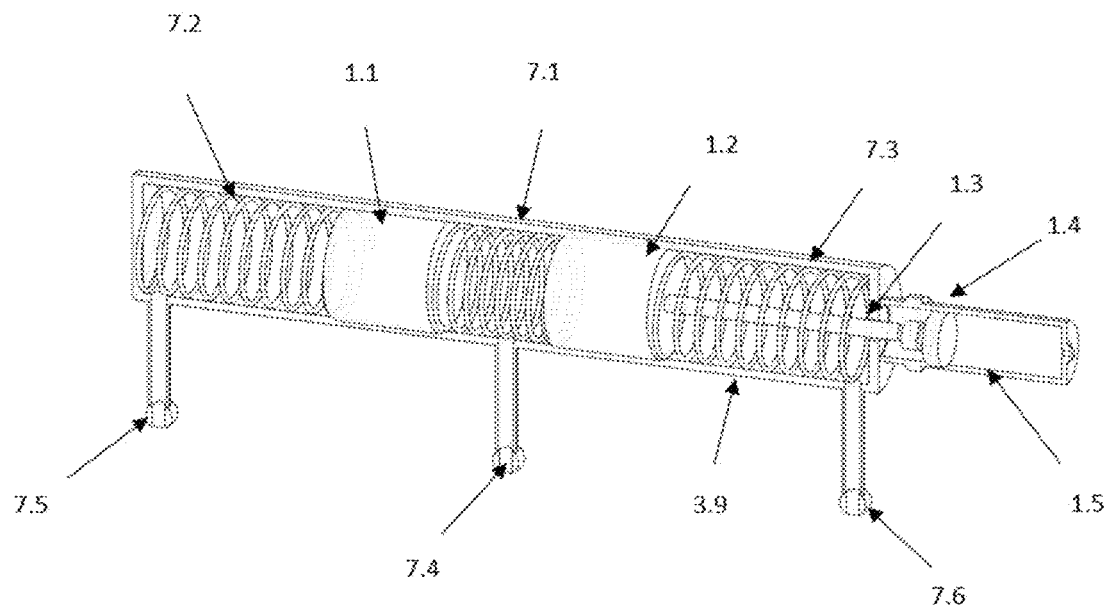
FIG. 7 depicts a schematic structural diagram of a needleless injection device according to an embodiment of the present invention when the first positioning spring is compressed.
Figure 8:
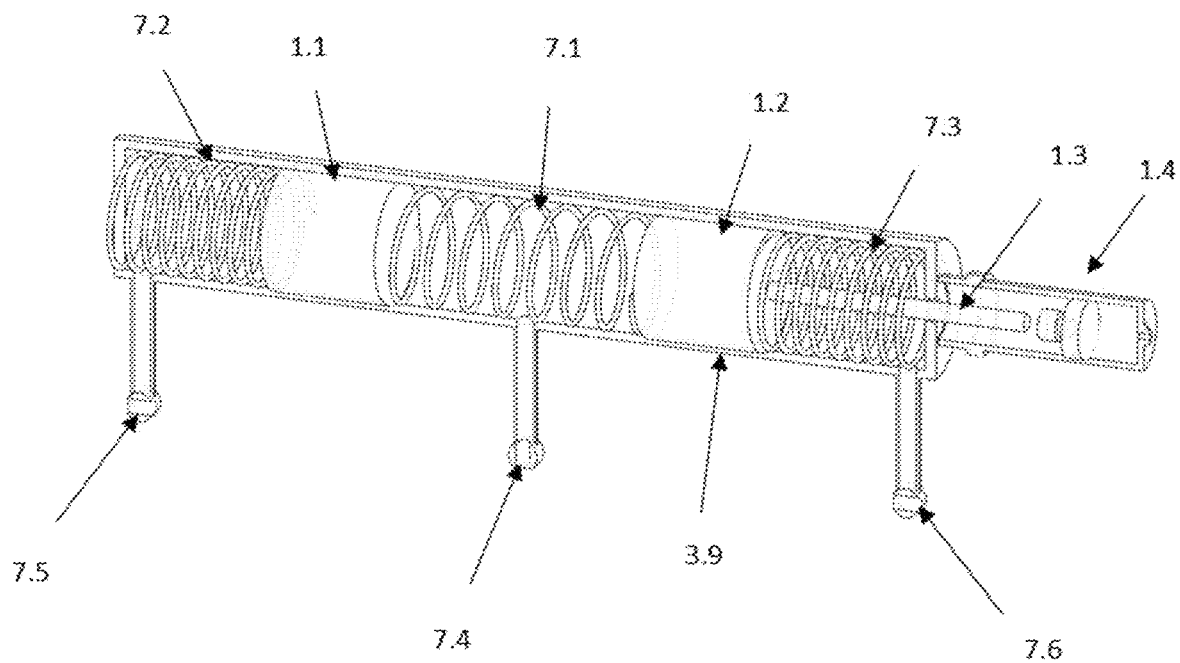
FIG. 8 depicts a schematic structural diagram of a needleless injection device according to another embodiment of the present invention when the first positioning spring is relaxed.

FIGS. 7 and 8 show an embodiment of a pneumatic controlled driving unit. The driving unit comprises a first positioning spring 7.1 positioned between a first slider 1.1 and a second slider 1.2, and a second positioning spring 7.2 between one end of the housing and the first slider 1.1, and a third positioning spring 7.3 positioned between the other end of the housing and the second slider 1.2. The space surrounding the first positioning spring 7.1 is configured to be in fluid communication with an inlet 7.4. The space surrounding the second positioning spring 7.2 is configured to be in fluid communication with the first outlet 7.5. The third positioning spring 7.3 is configured to be in fluid communication with a second outlet 7.6. The inlet 7.4 is used for receiving high-pressure gas. The first outlet 7.5 communicates with or connected with the second outlet 7.6.

The first, second and third positioning springs (7.1, 7.2 and 7.3) can restrict the movements of the first and second sliders (1.1 and 1.2) within or around the middle part of the needleless injection device body. All three positioning springs are attached to or restricted within the inside of injection body 3.9. When the injection device is used, high-pressure gas enters from the inlet 7.4, the first slider and the second slider (1.1, 1.2) are pushed outwards at the same time. The first slider and the second slider (1.1, 1.2) can move away from each other or move toward the opposite directions. The second slider 1.2 can drive the center injection shaft 1.3 to push the piston 1.4 of the ampoule injection tube 1.5. Then the piston 1.4 can push the liquid in the ampoule injection tube 1.5 to complete an injection step.

The gas at the space near the two ends of the injection body 3.9 can be compressed by the first and second sliders (1.1, 1.2), when the first and/or second outlets (7.5, 7.6) are closed. The compressed gas can be released through the first and second outlets (7.5, 7.6) when the first and second outlets (7.5, 7.6) are open. Further, the pressure can be increased to form an air cushion near both ends of the injection body 3.9, forming a gas cushion at each end of the injection body 3.9. Overall, the first, second, and third positioning springs (7.1, 7.2, 7.3) can buffer the impact force of the first and second sliders (1.1, 1.2), and the kinetic energy asserted by the sliders can be offset, so that the motion of the sliders can be stopped before the slider reaching the end of the injection body 3.9. Thus, the kinetic energy is not transmitted to the needleless injection. Finally, all the inlet and outlets (7.4, 7.5, 7.6) can be opened. The first and second sliders (1.1, 1.2) in the needleless injection device can be returned to the starting state.

In the process of the movement, the first, second, and third positioning springs (7.1, 7.2, 7.3), and the gas cushions at the two ends of the injection device body 3.9 can be automatically balanced by the controller, for example, by controlling the release of the compressed air from one of the gas cushions but not the other. Thus, the value of the combined momentum of the first and second sliders (1.1, 1.2) can be kept at substantially zero. Meanwhile, the elasticity of the second and third positioning springs 7.2 and 7.3 and the release of the gas from the first and second outlets (7.5, 7.6) can be adjusted, so that the value of the resulting momentum of the first and second sliders 1.1 and 1.2 can be adjusted to be substantially zero. A pneumatic driver can be implemented as a continuous driver, so that multiple injections are possible.

EXAMPLE 4

Figure 9:
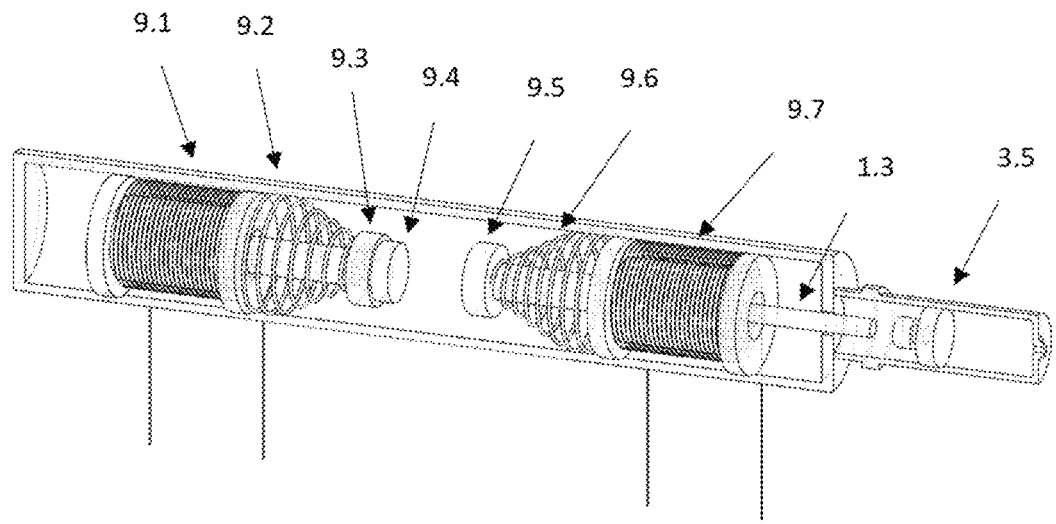
FIG. 9 is depicts a schematic structural diagram of a needleless injection device according to an embodiment of the present invention with an electromagnetic assembly before the electromagnetic assembly is activated.
Figure 10:
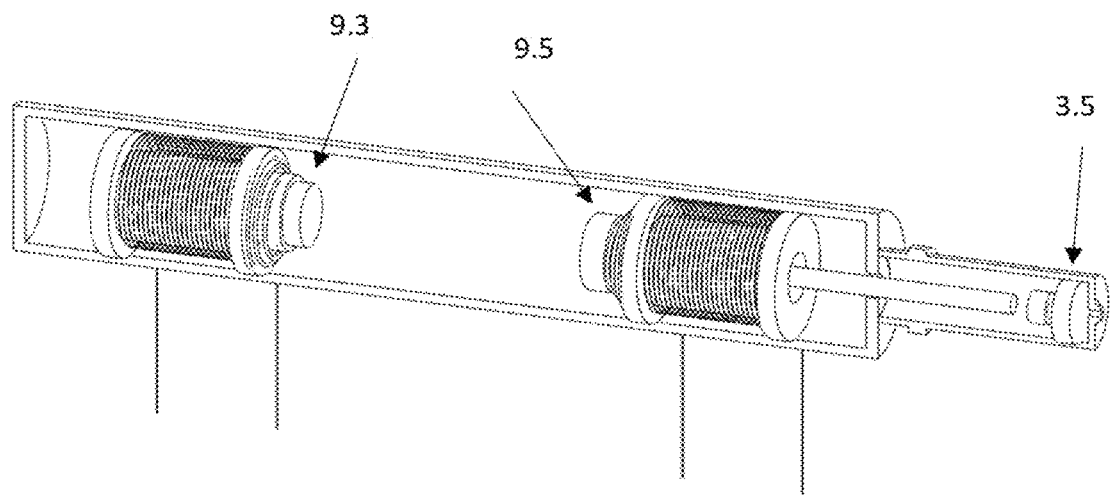
FIG. 10 depicts a schematic structural diagram of a needleless injection device according to an embodiment of the present invention with an electromagnetic assembly after the electromagnetic assembly is activated.

FIGS. 9 and 10 show an embodiment of an electromagnetic system to balance the momentum of the sliders. The driving unit can comprise a first electromagnet 9.1 affixed inside the housing and disposed at one end of the housing that is distal to the piston 3.5; a second electromagnet 9.7 affixed inside the housing and disposed at the other end of the housing proximal to the piston 3.5, thereby separating the first and second electromagnet (9.1, 9.7) by a fixed distance 9.4. Further, the first slider 1.1 comprises a first permanent magnetic core 9.3 with a first connection rod configured to slide through the hollow center of the first electromagnet 9.1; a first buffer spring 9.2 is disposed between the first permanent magnetic core 9.3 and the first electromagnet 9.1. The second slider 1.2 comprises a second permanent magnetic core 9.5 connected to the center injection shaft 1.3 through the hollow center of the second electromagnet 9.7; and a second buffer spring 9.6 is disposed between the second permanent magnetic core 9.5 and the second electromagnet 9.7. In this configuration, the first and second sliders (1.1, 1.2) including the first and second permanent magnetic cores (9.3, 9.5) can move within the restricted path defined by the fixed distance 9.4 between the first and second electromagnets (9.1, 9.7).

When the first and second electromagnets (9.1, 9.7) are powered, the first electromagnet 9.1 forms a magnet whose polarity is attractive to the first permanent magnetic core 9.3, while the second electromagnet 9.7 forms a magnet whose polarity is attractive to the second permanent magnetic core 9.5, thereby driving the first and second permanent magnetic cores (9.3, 9.5) to move outwards (i.e., away from each other and towards the first and second electromagnet, respectively). The center injection shaft 1.3 is then driven to push the piston 3.5 of the ampoule injection tube 1.5 by the outward movement of the second permanent magnetic cores (9.5), and the liquid in the ampoule injection tube 1.5 is squeezed to complete the injection. When the electrical power is shut off, the first and second buffer springs (9.2, 9.6) can help the first and second permanent magnetic cores (9.3, 9.5) to reset.

The combined momentum of the first and second permanent magnetic cores (9.3, 9.5) can be adjusted to be minimum by adjusting the elastic force of the first and second buffer springs (9.2, 9.6), adjusting the mass of the first and second permanent magnetic cores (9.3, 9.5) and adjusting the intensity of the electric current flowing through the wires of the electromagnet and the current starting and stopping time. Accordingly, by controlling the combined momentum of the first and second permanent magnetic cores (9.3, 9.5) the injection step may have the minimum impact on the needleless injection device body as a whole. The electromagnetic drive can be made continuous, so that multiple continuous needleless injections are possible.

EXAMPLE 5

Figure 11:
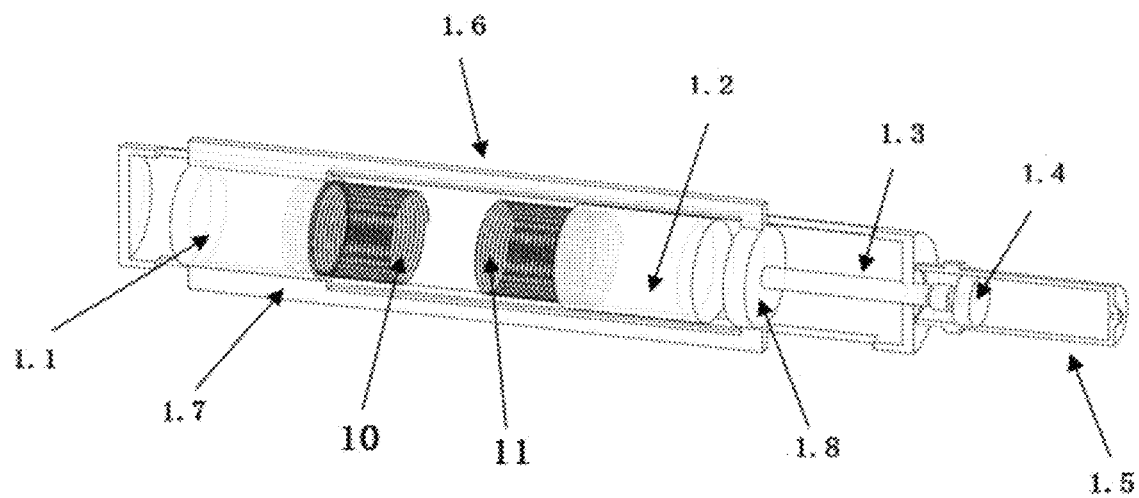
FIG. 11 depicts a schematic structural diagram of a needleless injection device according to an embodiment of the present invention with a voice coil before the voice coil is activated.
Figure 12:
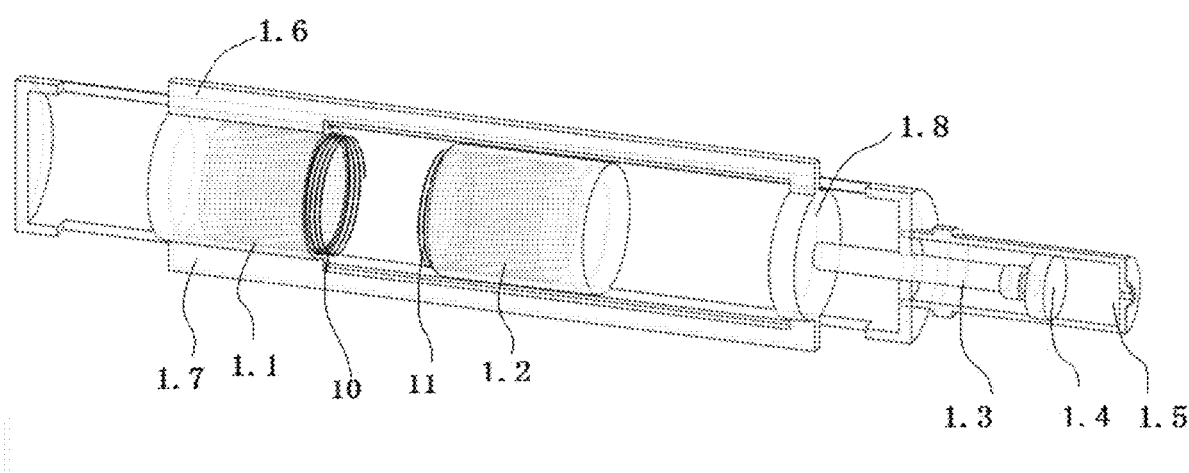
FIG. 12 depicts a schematic structural diagram of a needleless injection device according to an embodiment of the present invention with a voice coil after the electromagnetic assembly is activated.

FIGS. 11 and 12 show an example of another mechanical control using voice coil motor to balance the movements of the sliders. The driving system comprises a first voice coil 10 and a second voice coil 11; the first voice coil 10 is associated with the first slider 1.1 comprising a first permanent magnet element; the second voice coil 11 is associated with the second slider 1.2 comprising a second permanent magnet element; a connection disk 1.8 disposed inside the housing, between the second slider 1.2 and the ampoule injection tube 1.5, and connected with a center injection shaft 1.3 pointing toward the piston 1.4 which resides in the ampoule injection tube 1.5; an upper connection arm 1.6 connecting the connection disk 1.8 with the first slider 1.1; and a lower connection arm 1.7 connecting the connection disk 1.8 with the first slider 1.1. As disclosed above, each of the first slider 1.1 and the second slider 1.2 comprises a permanent magnet, respectively.

The voice coil motor is a linear motor which operates by utilizing the Lorentz force principle. It can control the running distance and the momentum of the first slider and the second slider (1.1, 1.2) accurately by controlling the magnitude of the electric current passing through the first and second voice coils (10, 11). In this embodiment, the first voice coil 10 and the second voice coil 11 are energized to form a voice coil motor. The voice coil motor then pushes the first permanent magnet element (i.e., the first slider 1.1) and the second permanent magnet element (i.e., the second slider) to move toward each other and toward the middle point of the housing. The first slider 1.1 drives the upper and lower connecting arms (1.6, 1.7) to move toward the ampoule injection tube 1.5, and further drives the connection disc 1.8 and the center injection shaft 1.3 to move towards the ampoule injection tube 1.5. When the center injection shaft 1.3 reaches and pushes the piston 1.4 of the ampoule injection tube 1.5, the liquid in the ampoule syringe 1.5 is squeezed to complete the injection (as shown in FIG. 12).

As disclosed above, the running distance and the momentum of the first and second sliders (1.1, 1.2) can be controlled by controlling the magnitude of the electric current passing through the first voice coil 10 and the second voice coil 11, so that the first and second sliders (1.1, 1.2) are driven by the two voice coil motors to move towards each other at the middle of the housing simultaneously. Accordingly, the resulting combined momentum of the first and second sliders (1.1, 1.2) can be reduced to the minimum or substantially zero.

EXAMPLE 6

Figure 13:
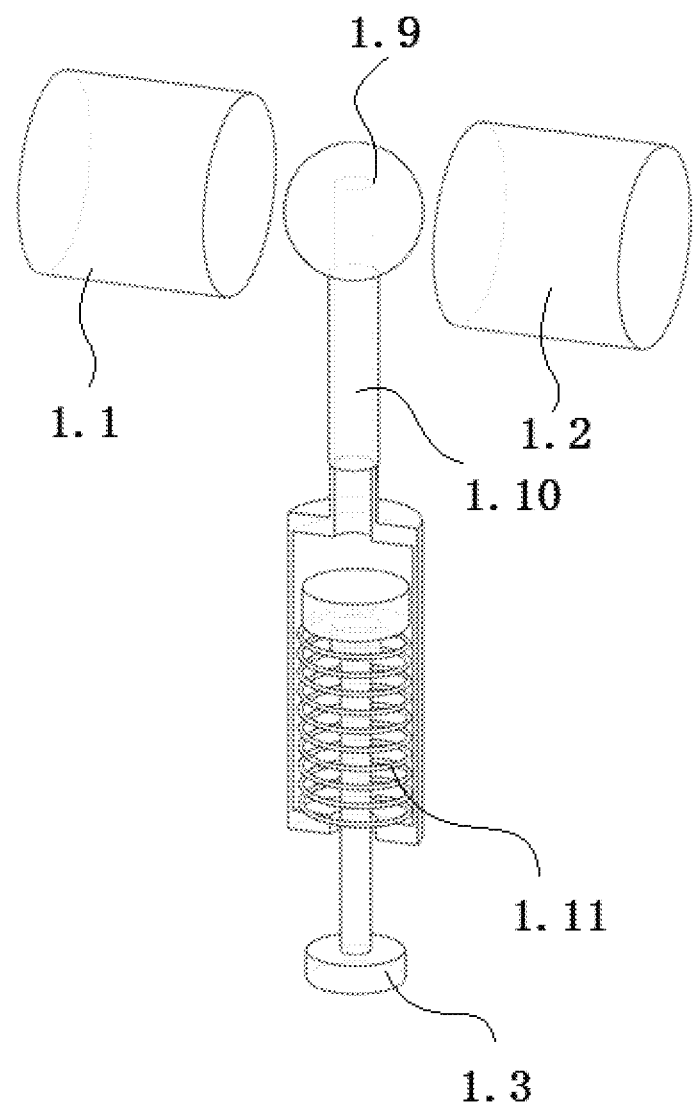
FIG. 13 depicts a schematic structural diagram of a needleless injection device according to an embodiment of the present invention with a pouch when the sliders rest.
Figure 14:
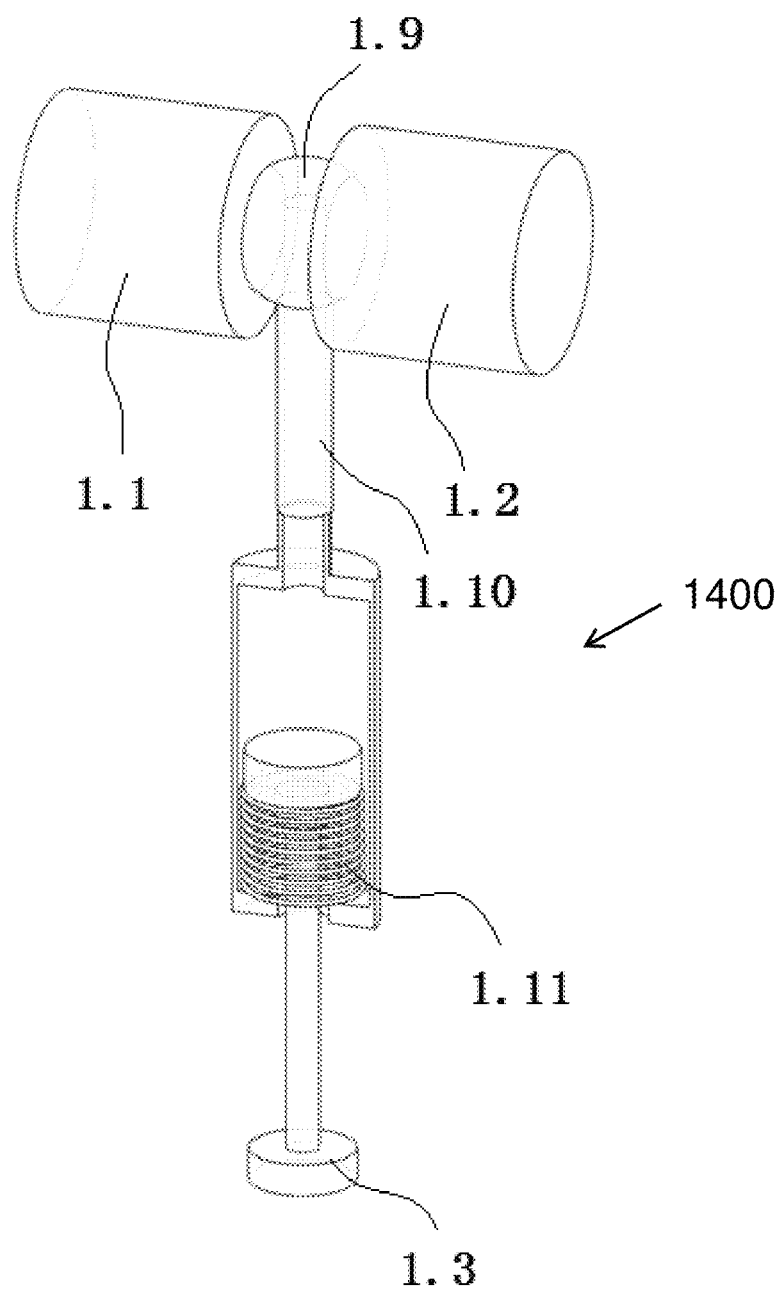
FIG. 14 depicts a schematic structural diagram of a needleless injection device according to an embodiment of the present invention with a pouch when the sliders are activated.

FIGS. 13 and 14 show an embodiment of a hydraulic pouch driving unit for a variety of mechanical balancing systems. The hydraulic pouch driving unit can adopt many mechanisms vide supra to bring the first and second sliders (1.1, 1.2) towards each other, such as, for example, the voice coil motor or others. The hydraulic pouch driving unit comprises a pouch 1.9; a conduit 1.10 connected with the pouch 1.19 via one end of the pouch 1.19; a reset spring 1.11 residing in and restricted within the conduit 1.10; and a center injection shaft 1.3 residing partially inside the conduit 1.11 in communication with the reset spring 1.11 and extending out of the conduit 1.11 through the other end of the conduit 1.10. The compressible pouch 1.9 is disposed between the first slider 1.1 and the second slider 1.2. The pouch 1.9 is connected with and in fluid communication with the conduit 1.10 through the end of the conduit 1.10. The conduit 1.10 also interacts with the center injection shaft 1.3 which interacts with the reset spring 1.11 as shown in FIGS. 13 and 14. Pouch 1.9 is filled with a fluid. When the pouch 1.9 expands or is compressed, the fluid in pouch 1.9 can flow downward toward the conduit 1.10 since the pouch is in fluid communication with the conduit 1.10. The hydraulic power of the fluid can also change, thereby changing the position of center injection shaft 1.3.

The first slider 1.1 and the second slider 1.2 of the needleless injection device 1400 can move toward each other under the control of a mechanical balancing system to compress the pouch 1.9 (FIG. 14). By doing so most kinetic energy from the first and second sliders (1.1, 1.2) is transferred into the momentum of the fluid flowing out of the pouch 1.9. Liquid can flow in any directions out of the pouch following the guide of the outflow port toward the conduit 1.10. The momentum of the flowing liquid can be used to push the center injection shaft 1.3 downward. In turn the center injection shaft 1.3 can push the piston 1.4 of the ampoule injection tube 1.5, forcing out the liquid in the ampoule injection tube 1.5 to complete the injection. Since the conduit 1.10 can adopt different orientations relative to the moving axis of the first and second sliders (1.1, 1.2) and the position of the pouch 1.9, the direction of the injection can be set accordingly, for example, to more than one directions. This can be done by adjusting the connection tube between the pouch 1.9 and the end of the conduit 1.10.

EXAMPLE 7

Figure 15:
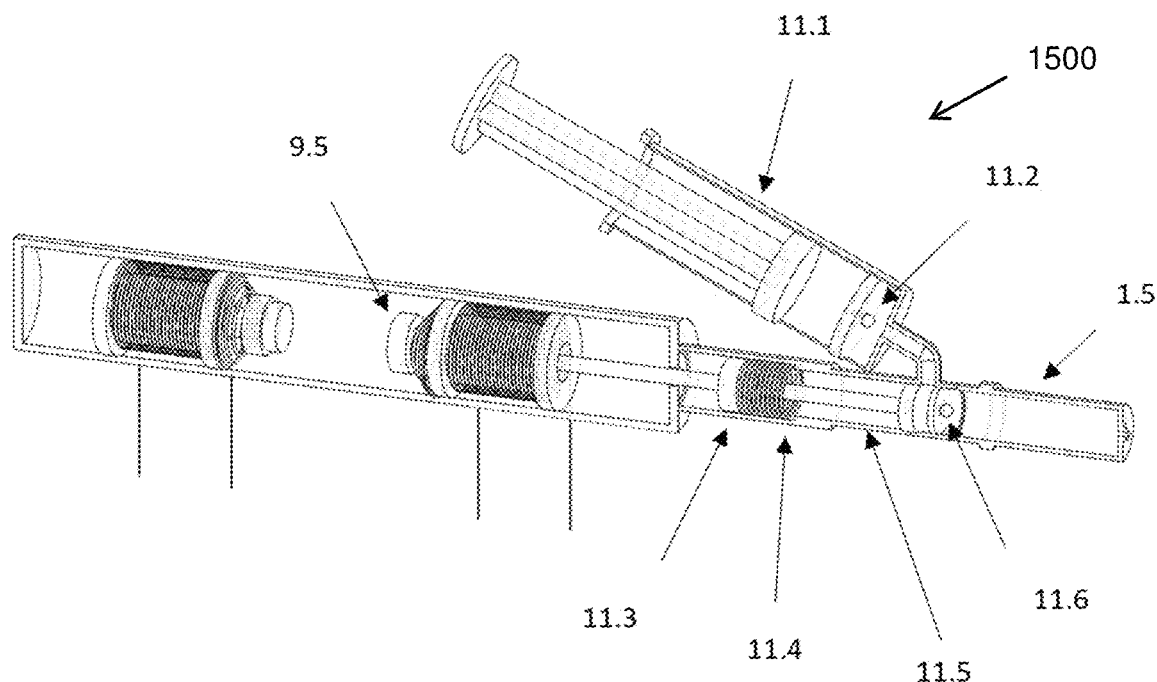
FIG. 15 depicts a schematic structural diagram of a needleless injection device according to another embodiment of the present invention with an electromagnetic assembly having a liquid storage container.

Driving unit of the electrical system using a compression spring (Example 2), the pneumatic controlled driving unit (Example 3), the electromagnetic system (Example 4), and the like, can be harnessed to provide power to continuous needleless injection devices. FIG. 15 presents an embodiment of a continuous needleless injection device 1500 equipped with an electromagnetic system as the driving unit.

As shown in FIG. 15, the continuous needleless injection device 1500 comprises a medicine storage container 11.1, a resettable measurement container 11.5, a shaft 11.3 for resettable measurement container 11.5, a resetting spring 11.4 for the shaft for measurement container 11.3, a first check valve 11.2 for the medicine storage container 11.1, and a second check valve 11.6 for the resettable measurement container 11.5, in addition to the first and second sliders (1.1, 1.2), the ampoule injection tube 1.5, etc.

When the device is in operation, the shaft 11.3 for the resettable measurement container 11.5 is push to a predetermined position within the chamber of the resettable measurement container 11.5, and a predetermined amount of the liquid in the medicine storage container 11.1 is allowed to be pumped into the chamber of the resettable measurement container 11.5 through the first check valve 11.2 of the medicine storage container 11.1. When the shaft 11.3 of the resettable measurement container is struck and pushed forward (i.e., by the momentum of the second slider 1.2), the liquid in the chamber of the resettable measurement container 11.5 is squeezed into the ampoule injection tube 1.5 through the second check valve 11.6, and the liquid is injected into the subject, thereby completing an injection cycle. By adjusting the position of the shaft 11.3 within the resettable measurement container 11.5, the injected amount/volume of the liquid can be adjusted. The continuous injection can be accomplished by combining the electrical system using a compression spring (Example 2), the pneumatic controlled driving unit (Example 3), the electromagnetic system (Example 4) as the driving unit to control the shaft 11.3 or the medicine storage container.

EXAMPLE 8

Figure 16:
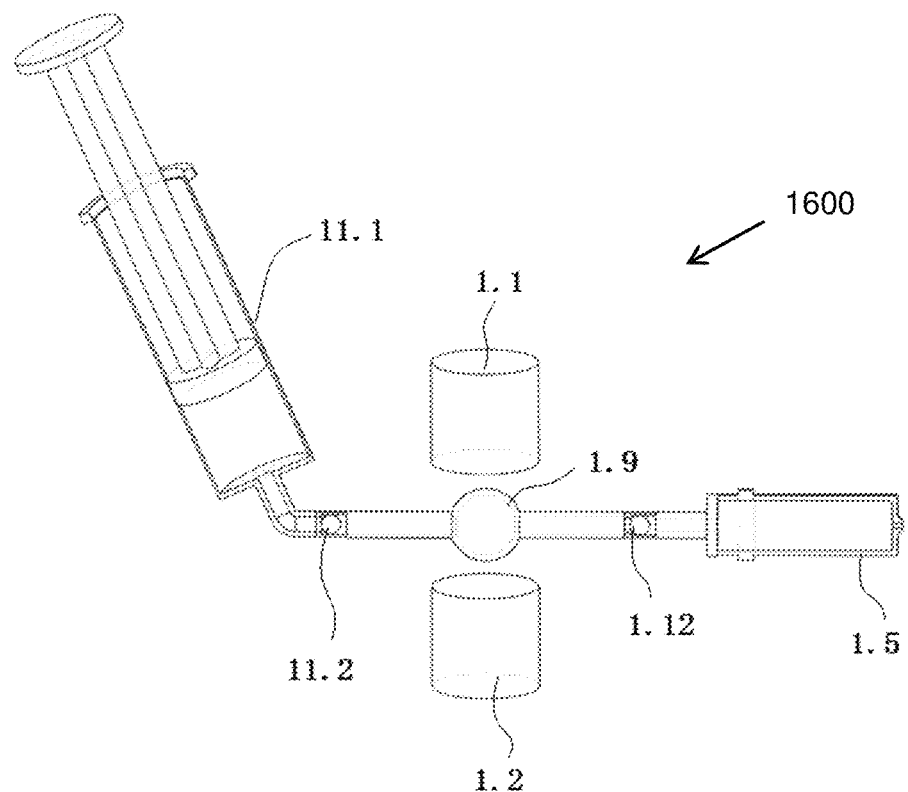
FIG. 16 depicts a schematic structural diagram of a needleless injection device according to an embodiment of the present invention with a pouch configuration for performing multiple sequential injections.

As shown in FIG. 16, another embodiment of the continuous needleless injection device is shown. In this embodiment, the first slider 1.1 and the second slider 1.2 can be driven to push a hydraulic pouch driving unit (Example 6). The first and second sliders can be driven by the electrical system using a compression spring (Example 2), the pneumatic controlled driving unit (Example 3), the electromagnetic system (Example 4), and the like.

The continuous needleless injection device 1600 comprises a first slider 1.1, a second slider 1.2, a hydraulic pouch driving unit comprising a pouch 1.9, a third check valve 1.12 for the pouch 1.9, a first check valve 11.2 (for medicine storage container 11.1), an ampoule injection tube 1.5 and the like.

The pouch 1.9 is connected with a first conduit and second conduit. The first conduit is connected with the medicine storage container 11.1 through the first check valve 11.2. The second conduit is connected with the ampoule injection tube 1.5 through the third check valve 1.12 for the pouch 1.9. When the first and second sliders (1.1, 1.2) rest, the pouch 1.9 is not pressed and can accept/store the liquid from the medicine storage container 11.1 via the first check valve. The pouch 1.9 can expand after receiving the liquid from the medicine storage container 11.1. When the first and second sliders (1.1, 1.2) are in operation and pressing the pouch 1.9, the liquid stored in the pouch 1.9 can be pressurized, and the liquid in the pouch 1.9 can enter the ampoule injection tube 1.5 through the third check valve 1.12. The liquid entering the ampoule injection tube 1.5 can be injected into a subject later or concurrently.

EXAMPLE 9

Figure 17:
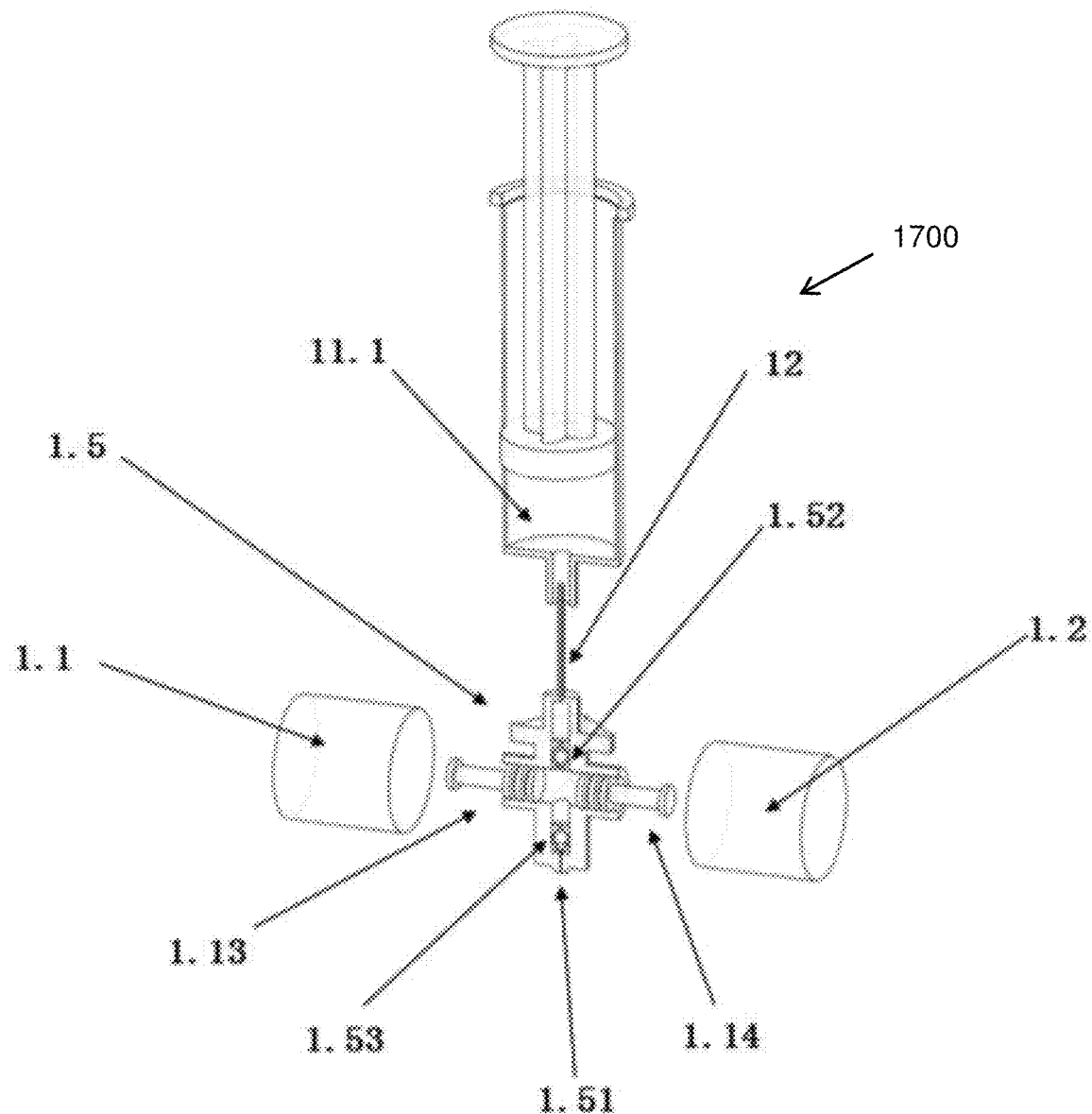
FIG. 17 depicts a schematic structural diagram of a continuous needleless injection device according to an embodiment of the present invention with an ampoule for multiple continuous injections.

FIG. 17 shows another embodiment of the continuous needleless injection device with similarities to the device 1600 in FIG. 16. The continuous needleless injection device 1700 comprises an ampoule injection tube 1.5, a left striking core 1.13, a right striking core 1.14, the left and right striking cores (1.13 and 1.14) being configured to be placed on opposite sides of the ampoule injection tube 1.5, to engage with and to be in fluid communication with the chamber of the ampoule injection tube 1.5, an upper check valve 1.52, a lower check valve 1.53, the upper and lower check valves configured to engage with and to be in fluid communication with the chamber of the ampoule injection tube 1.5, an ampoule injection port 1.51, the first slider 1.1, the second slider 1.2, a medicine storage container 11.1 and a conduit 12. The upper check valve 1.52 is in fluid communication with the medicine storage container 11.1 through the conduit 12. The lower check valve 1.53 is in fluid communication with the ampoule injection port 1.51.

The left striking core 1.13 and the right striking core 1.14 can be engaged with the first slider 1.1 and the second slider 1.2, respectively. Hence, the left striking core 1.13 is configured to be driven by the first slider 1.1. The right striking core 1.14 is configured to be driven by the second slider 1.2. When the first and second sliders (1.1, 1.2) are engaged with and pressing the left and right striking cores (1.13, 1.14), respectively, the liquid stored in the chamber of the ampoule injection tube 1.5 can be forced to move downward via the lower check valve 1.53. The liquid thus released from the chamber of the ampoule injection tube 1.5 can be injected into a subject, thereby completing the injection.

When the first and second sliders (1.1, 1.2) rest, the left striking core 1.13 and the right striking core 1.14 can be configured to move outward for predetermined distance with regard to the chamber, thereby decreasing the inner pressure of the chamber. The upper check valve 1.52 can be opened and the lower check valve 1.53 can be closed, thereby allowing liquid stored in the medicine storage container 11.1 to enter the chamber of the ampoule injection tube 1.5 via conduit 12. When the first and second sliders (1.1, 1.2) are engaged with and pressing the left and right striking cores (1.13, 1.14) again, another injection can be accomplished.

The continuous injection can be accomplished by repeating the above loading and injecting steps repeatedly. By controlling the outward movements of the left striking core 1.13 and the right striking core 1.14 relative to the chamber of the ampoule injection tube 1.5, the amount of liquid entering the chamber at each loading step can be controlled, thereby the amount of the liquid injected is also controllable.

EXAMPLE 10

Figure 18:
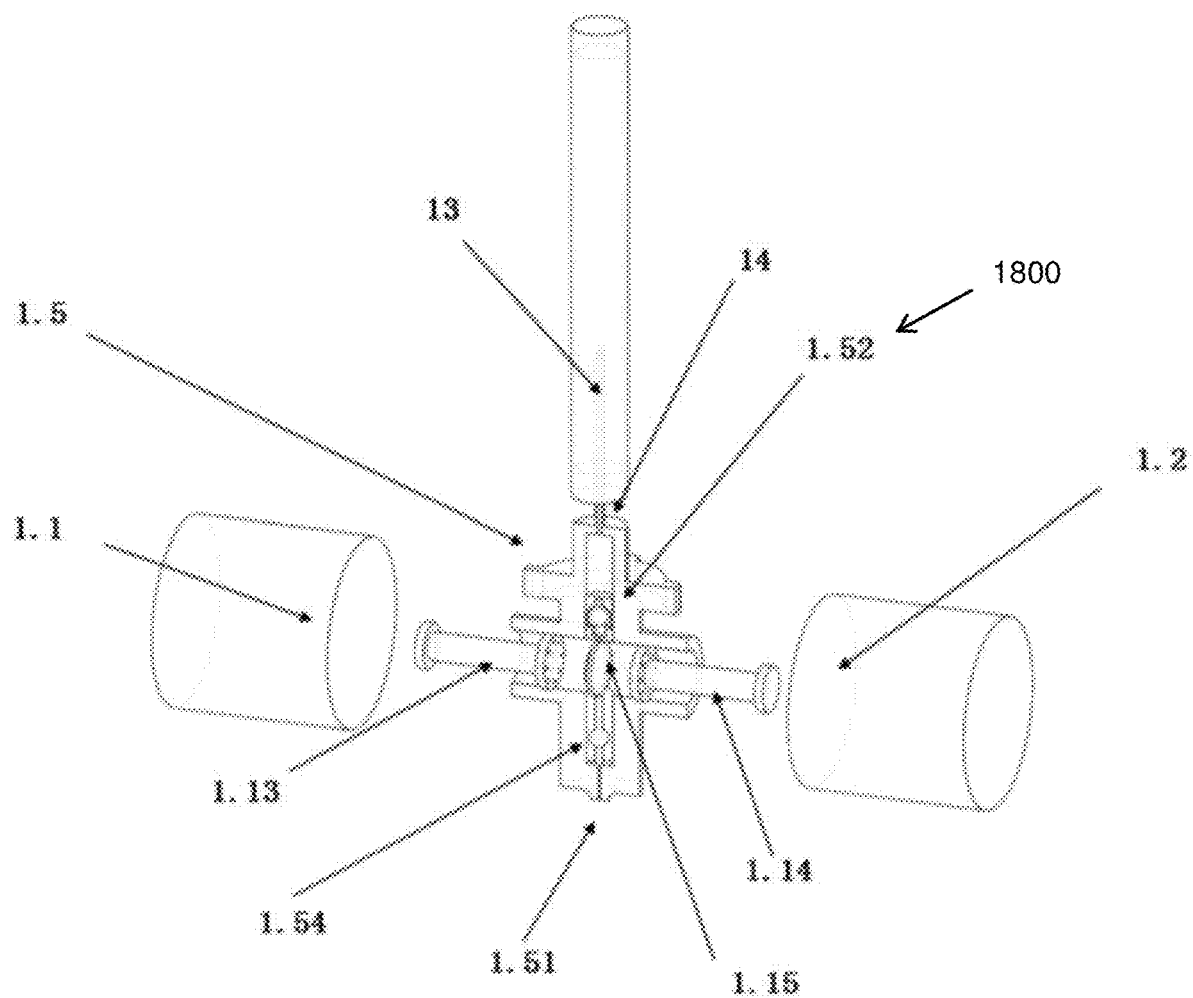
FIG. 18 depicts a schematic structural diagram of a continuous needleless injection device according to another embodiment of the present invention with an ampoule comprising an expandable pouch for multiple continuous injections.

FIG. 18 shows still another embodiment of the continuous needleless injection device with similarities to the device 1600 in FIG. 16. The continuous needleless injection device 1800 comprises an ampoule injection tube 1.5, a left striking core 1.13, a right striking core 1.14, the left and right striking cores (1.13 and 1.14) being configured to be placed on opposite sides of the ampoule injection tube 1.5, to engage with and to be in fluid communication with the an expandable pouch 1.15, an upper check valve 1.52, a pressure-limit valve 1.54 residing in the chamber of the ampoule injection tube 1.5 and configured to be in fluid communication with the expandable pouch 1.15, the upper check valve 1.52 and the pressure-limit valve 1.54 configured to engage with and to be in fluid communication with the expandable pouch 1.15, an ampoule injection port 1.51, the first slider 1.1, the second slider 1.2, a liquid storage container 13, and a needle 14. The upper check valve 1.52 is in fluid communication with the liquid storage container 13 through the needle 14. The pressure-limit valve 1.54 is in fluid communication with the ampoule injection port 1.51. The expandable pouch 1.15 is in fluid communication with the upper check valve 1.52 and the pressure-limit valve 1.54.

The left striking core 1.13 and the right striking core 1.14 can be engaged with the first slider 1.1 and the second slider 1.2, respectively. Hence, the left striking core 1.13 is configured to be driven by the first slider 1.1. The right striking core 1.14 is configured to be driven by the second slider 1.2. When the first and second sliders (1.1, 1.2) are engaged with and pressing the left and right striking cores (1.13, 1.14), respectively, the liquid stored in the expandable pouch 1.15 inside the chamber of the ampoule injection tube 1.5 can be forced to move downward via the pressure-limit valve 1.54 when the pressure inside the expandable pouch exceeds the pressure limit of the pressure-limit valve. The liquid thus released from the expandable pound 1.15 inside the chamber of the ampoule injection tube 1.5 can be injected into a subject, thereby completing the injection.

When the first and second sliders (1.1, 1.2) rest, the operator can operate the liquid storage container 13, release a predetermined amount of liquid into the expandable pouch 1.15 via the upper check valve 1.52. The expandable pouch can expand such that the pressure inside the pouch is lower than the pressure limit for the pressure-limit valve. Thus, when the liquid is loaded into the expandable pouch, the pressure-limit valve is closed. However, when the first and second sliders (1.1, 1.2) are engaged with and pressing the left and right striking cores (1.13, 1.14), respectively, the pressure inside the expandable pouch can increase and exceed the pressure limit set for the pressure-limit valve, thereby opening the pressure-limit valve.

The continuous injection can be accomplished by repeating the above loading and injecting steps repeatedly.

As shown above, the present method can eliminate recoil actions in needleless injection. The present invention can solve the problem of undesirable recoil actions in the process of injecting liquid using needless injection devices and reduce/avoid the uncomfortable impact by the recoiling injection device on the subject.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A needleless injection device, comprising:
   a housing;
   a first slider disposed in the housing and movable along an axis;
   a second slider disposed in the housing and movable along the axis;
   an ampoule injection tube; and
   a driving unit configured to move the first slider and the second slider in opposite directions along the axis, characterized in that the value of the combined momentum of the first slider and the second slider is substantially zero under the control of the driving unit,
   wherein the driving unit further comprises:
      a first electromagnet affixed inside the housing and disposed between the first slider and one end of the housing; and
      a second electromagnet affixed inside the housing and disposed between the second slider and the other end of the housing, thereby the first slider and the second slider are disposed between the first electromagnet and the second electromagnet;
   wherein the first slider comprises a first permanent magnetic core with a first connection rod configured to slide through a hollow center of the first electromagnet;
   wherein a first buffer spring is disposed between the first permanent magnetic core and the first electromagnet;
   wherein the second slider comprises a second permanent magnetic core connected to a center injection shaft through a hollow center of the second electromagnet; and
   wherein a second buffer spring is disposed between the second permanent magnetic core and the second electromagnet.

2. The needless injection device of claim 1, further comprising:
   a piston configured to slide inside the ampoule injection tube and interact with the first slider, the second slider, or both the first and second slider.

3. The needleless injection device of claim 2, wherein the center injection shaft is configured to interact with the piston, and wherein the center injection shaft is configured to contact the piston when the second slider moves away from the first slider.

4. The needleless injection device of claim 2, wherein the ampoule injection tube is along the axis, and wherein the second slider is positioned between the first slider and the piston.

5. The needleless injection device of claim 1, wherein the ampoule injection tube is not along the axis.

* * * * *